(12) United States Patent
DiPrete et al.

(10) Patent No.: US 10,145,965 B1
(45) Date of Patent: Dec. 4, 2018

(54) QUANTITATIVE RADIOACTIVITY MONITOR FOR ASSAYS OF WILDLIFE

(71) Applicant: Savannah River Nuclear Solutions, LLC, Aiken, SC (US)

(72) Inventors: David P. DiPrete, Evans, GA (US); Tad S. Whiteside, Aiken, SC (US); Donald J. Pak, Martinez, GA (US); Timothy J. Aucott, Aiken, SC (US); Alexander D. Brand, Augusta, GA (US); Teresa P. Eddy, Trenton, SC (US); Karen M. Vangelas, Aiken, SC (US)

(73) Assignee: SAVANNAH RIVER NUCLEAR SOLUTIONS, LLC, Aiken, SC (US)

( * ) Notice: Subject to any disclaimer, the term of this patent is extended or adjusted under 35 U.S.C. 154(b) by 0 days.

(21) Appl. No.: 15/813,352

(22) Filed: Nov. 15, 2017

(51) Int. Cl.
  *G01T 1/16* (2006.01)
  *G01T 1/163* (2006.01)
  *A61B 6/00* (2006.01)
  *G01T 1/29* (2006.01)
  *G01T 1/18* (2006.01)

(52) U.S. Cl.
  CPC ............ *G01T 1/163* (2013.01); *A61B 6/4021* (2013.01); *A61B 6/4233* (2013.01); *A61B 6/4241* (2013.01); *G01T 1/18* (2013.01); *G01T 1/2985* (2013.01)

(58) Field of Classification Search
  CPC ......... G01T 1/163; G01T 1/18; G01T 1/2985; A61B 6/4021; A61B 6/4233; A61B 6/4241
  See application file for complete search history.

(56) References Cited

U.S. PATENT DOCUMENTS 4,862,004 A * 8/1989 Koike .................. G01T 1/40
                                                    250/369
2010/0268077 A1* 10/2010 Nakamura ............. A61B 6/032
                                                    600/436
(Continued)

OTHER PUBLICATIONS

Accuscan™ Horizontal Bed Whole Body Counter, www.canberra.com/products/hp_radioprotection/accuscan.asp, copyright 2017, all pages.
(Continued)

*Primary Examiner* — Marcus Taningco
(74) *Attorney, Agent, or Firm* — Dority & Manning, PA

(57) ABSTRACT

The present disclosure is directed to a detection assembly for detecting radiation emitted by radionuclides present within an animal. The detection assembly includes a housing having one or more walls defining a chamber. The detection assembly also includes a cover removably positioned over the top end of the housing, with the cover being configured for receipt of the animal. Furthermore, the detection assembly includes a radiation sensor positioned within the chamber. The radiation sensor is configured to detect the radiation emitted by the radionuclides present within the animal. Additionally, the detection assembly includes a shield positioned around a first portion of the radiation sensor, with the shield being configured to at least partially shield the radiation sensor from environmental radiation. A second portion of the radiation sensor is unshielded to permit the radiation sensor to receive radiation emitted by the radionuclides present within the animal.

9 Claims, 8 Drawing Sheets

(56) References Cited

U.S. PATENT DOCUMENTS

2014/0058187 A1* 2/2014 Groke .................. A61N 5/1071
600/3
2017/0245811 A1* 8/2017 Hernandez ............... A61B 6/10

OTHER PUBLICATIONS

AT1316 Whole Body Counter, www.atomex.com/en/products/whole-body-counters/at 316-whole-body-counter, all pages.
WBC-BSCAN Whole Body Scanning Bed www.ortec-online.com/products/radiochemistry-health-physics-research-industrial all pages.

* cited by examiner

QUANTITATIVE RADIOACTIVITY MONITOR FOR ASSAYS OF WILDLIFE

FEDERAL RESEARCH STATEMENT

This invention was made with Government support under Contract No. DE-AC09-085R22470, awarded by the U.S. Department of Energy. The Government has certain rights in the invention.

FIELD OF THE INVENTION

The present disclosure generally relates to the detection of radiation emitted by animals. More particularly, the present disclosure relates to detection assemblies for detecting radiation emitted by radionuclides present within animals and associated systems for determining a radiation dose present within the animals.

BACKGROUND OF THE INVENTION

Certain species of animals, such as deer, are routinely hunted to maintain a healthy population. The meat from these animals may then be consumed by the hunter or other persons. However, if these animals live near nuclear power facilities or other sources of man-made radiation, their meat may contain elevated levels of certain radionuclides, such as cesium-137. The consumption of meat containing such elevated levels of radionuclides may lead to various short- and long-term health problems.

In order to prevent hunters or other people from consuming meat with high levels of radioactivity, the radiation dose present within animals hunted near nuclear facilities should be checked before the animal is processed and consumed. However, conventional devices for detecting radiation emitted by animals are unable to detect radiation levels below a certain value. Although a single dose of such low levels of radiation may not cause health effects, several doses of these low levels of radiation received over a period time may lead to health problems. Furthermore, conventional systems for determining an associated radiation dose within the animals do not take into account the geometry of the animals, thereby providing inaccurate results.

Accordingly, an improved detection assembly for detecting and measuring radiation emitted by radionuclides present within animals and an associated system for determining a radiation dose present within the animals would be welcomed in the art.

BRIEF DESCRIPTION OF THE INVENTION

Aspects and advantages of the invention will be set forth in part in the following description, or may be apparent from the description, or may be learned through practice of the invention.

In one aspect, the present disclosure is directed to a detection assembly for detecting radiation emitted by radionuclides present within an animal. The detection assembly includes a housing extending along a vertical direction between a top end and a bottom end. The housing includes one or more walls defining a chamber within the housing. The top end of the housing is at least partially open. The detection assembly also includes a cover removably positioned over the top end of the housing, with the cover being configured for receipt of the animal. Furthermore, the detection assembly includes a radiation sensor positioned within the chamber. The radiation sensor is configured to detect the radiation emitted by the radionuclides present within the animal. Additionally, the detection assembly includes a shield positioned around a first portion of the radiation sensor, with the shield being configured to at least partially shield the radiation sensor from environmental radiation. A second portion of the radiation sensor is unshielded to permit the radiation sensor to receive radiation emitted by the radionuclides present within the animal.

In another aspect, the present disclosure is directed to a system for measuring concentrations of gamma ray-emitting radionuclides present within an animal and determining a radiation dose one would receive when consuming the animal. The system includes a radiation sensor configured to detect or measure radiation emitted by radionuclides present within the animal. The radiation sensor includes a first portion at least partially shielded from environmental radiation. The radiation sensor further includes a second portion that is unshielded to permit the radiation sensor to receive the radiation emitted by the radionuclides present within the animal. The system also includes a controller communicatively coupled to the radiation sensor. The controller is configured to receive a non-geometric parameter indicative of a characteristic of the animal and determine a geometric parameter of the animal based on the non-geometric parameter. The controller is further configured to determine a concentration of gamma ray-emitting radiological isotopes present within the animal based on the non-geometric parameter, the geometric parameter, and measurement signals received from the radiation sensor.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
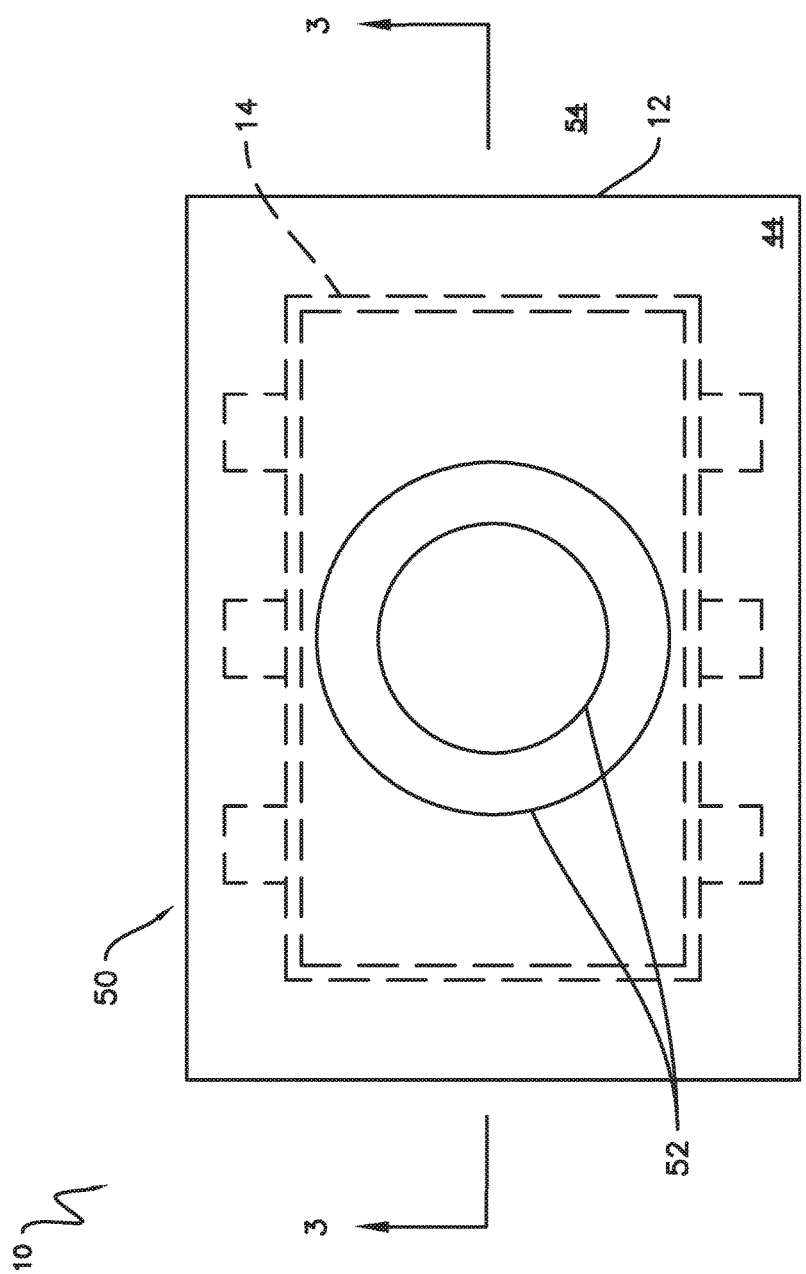
FIG. 1 is a top view of one embodiment of a detection assembly for detecting radiation emitted by radionuclides present within an animal in accordance with aspects of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 2:
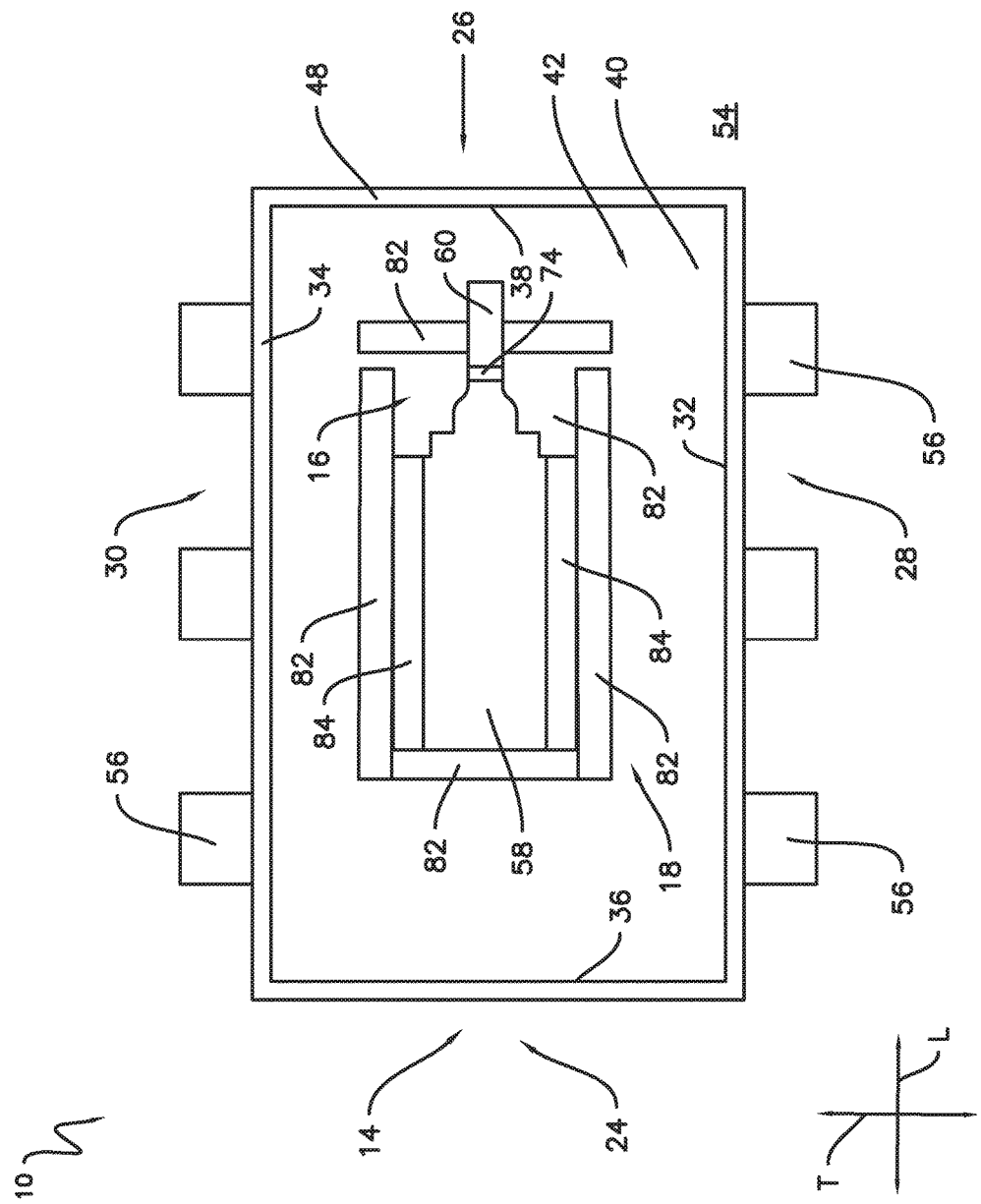
FIG. 2 is another top view of the embodiment of the detection assembly shown in FIG. 1, particularly illustrating a radiation sensor and a shield of the detection assembly.
Figure 3:
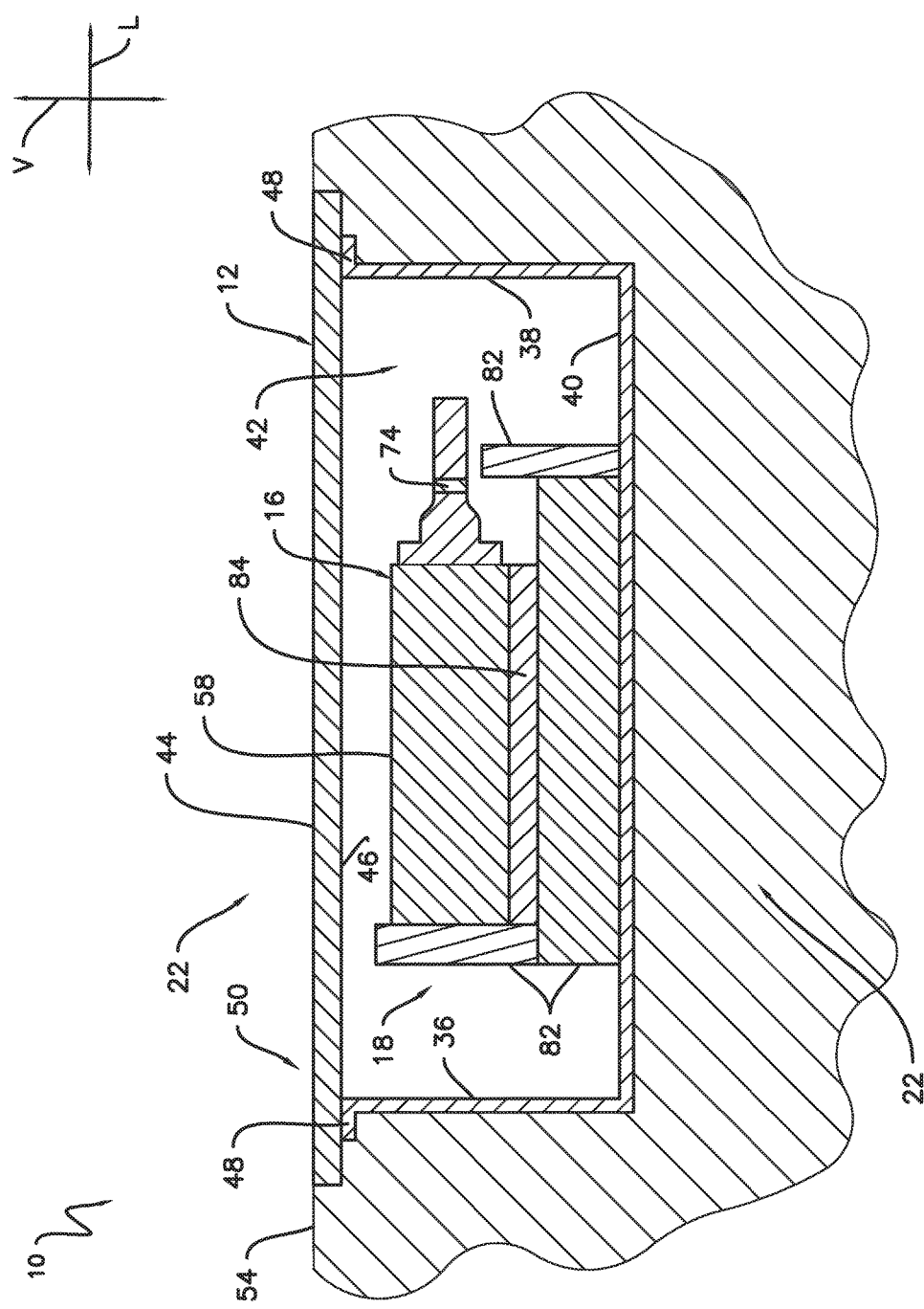
FIG. 3 is a cross-sectional view of the detection assembly taken generally about line 3-3 in FIG. 1, further illustrating the radiation sensor and the shield.
Figure 4:
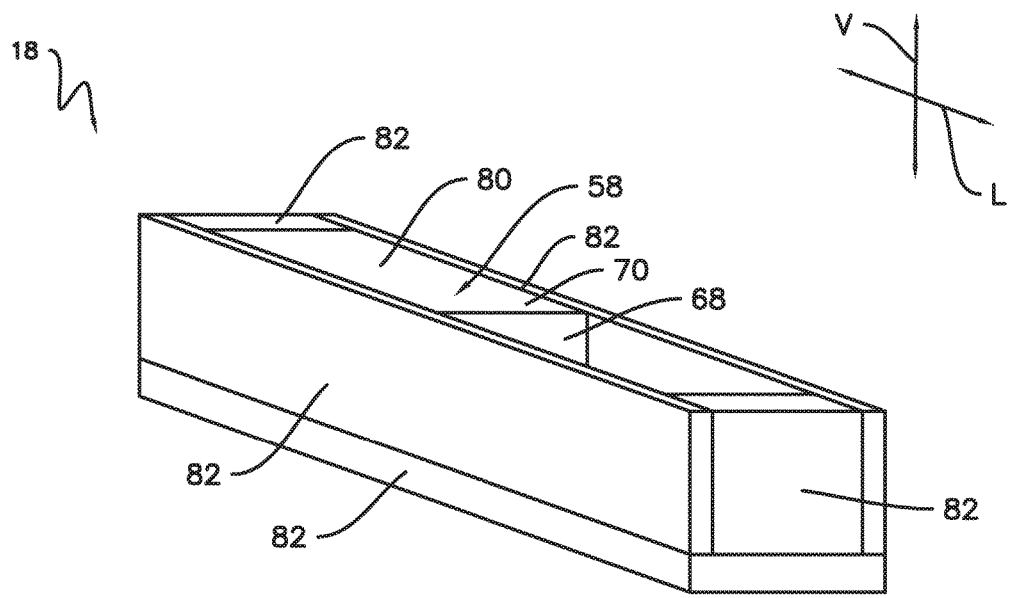
FIG. 4 is a perspective view of one embodiment of a shield in accordance with aspects of the present disclosure, particularly illustrating the relative positioning of a radiation sensor within the shield.

Referring now to drawings, FIGS. 1 through 3 illustrate differing views of one embodiment of a detection assembly 10 for detecting radiation emitted by radionuclides present within an animal in accordance with aspects of the present disclosure. Specifically, FIG. 1 is a top view of the detection assembly 10, illustrating a cover 12 positioned on a housing 14. FIG. 2 is another top view of the detection assembly 10 with the cover 12 removed from the housing 14 to illustrate a radiation sensor 16 and a shield 18 of the detection assembly 10. Additionally, FIG. 3 is a cross-sectional view of the detection assembly 10, further illustrating the radiation sensor 16 and the shield 18.

In general, the housing 14 may define a vertical direction V, a lateral direction L orthogonal to the vertical direction V, and a transverse direction T orthogonal to the vertical direction V and the longitudinal direction L. More specifically, the housing 14 may extend along the vertical direction V between a top end 20 of the housing 14 and a bottom end 22 of the housing 14. The housing 14 may also extend along the longitudinal direction L between a first longitudinal end 24 of the housing 14 and a second longitudinal end 26 of the housing 14. Furthermore, the housing 14 may extend along the traverse direction T between a first traverse end 28 of the housing 14 and a second traverse end 30 of the housing 14.

As shown, the housing 14 includes various walls. For example, the housing 14 may include a first longitudinally-extending wall 32 positioned at the first transverse end 28 of the housing 14 and a second longitudinally-extending wall 34 positioned at the second transverse end 30 of the housing 14 and transversely spaced apart from the first longitudinally-extending wall 32. Similarly, the housing 14 may include a first transversely-extending wall 36 positioned at the first longitudinal end 24 of the housing 14 and a second transversely-extending wall 38 positioned at the second longitudinal end 26 of the housing 14 and longitudinally spaced apart from the first transversely-extending wall 36. Furthermore, the housing 14 may include a bottom wall 40 positioned at the bottom end 22 of the housing 14. As such, in the illustrated embodiment, the housing 14 defines a rectangular cross-section. Nevertheless, in alternative embodiments, the housing 14 may include other walls in addition to or in lieu of the walls 32, 34, 36, 38, 40 and/or define a different cross-section. Furthermore, in one embodiment, the housing 14 is constructed from stainless steel. Although, the housing 14 may be formed from any other suitable material, such as another suitable metallic material.

The various walls 32, 34, 36, 38, 40 of the housing 14 may define a chamber 42 within the housing 14 for receiving the radiation sensor 16 and the shield 18. In the illustrated embodiment, for example, the chamber 42 may be defined transversely between the first longitudinally-extending wall 32 and the second longitudinally-extending wall 34. The chamber 42 may also be defined longitudinally between the first transversely-extending wall 36 and the second transversely-extending wall 38. Furthermore, the chamber 42 may be defined vertically between the bottom wall 40 and the top end 20 of the housing 14. As shown in FIG. 3, the housing 14 may be at least partially open at the top end 20 thereof to permit access to the chamber 42.

As indicated above, the detection assembly 10 also includes the cover 12. In particular, the cover 12 may include a top surface 44 and a bottom surface 46 vertically spaced apart from the top surface 44. In general, the cover 12 is removably positioned on the top end 20 of the housing 14 such that the bottom surface 46 of the cover 12 is positioned on or otherwise in contact with the top end 20 of the housing 14. For example, in one embodiment, the housing 14 may include one or more flanges 48 extending outwardly (i.e., away from the chamber 42) from one or more of the walls 32, 34, 36, 38 to support the cover 12. In this respect, the cover 12 and the housing 14 may collectively form an enclosure 50 in which the radiation sensor 16 and the shield 18 are positioned. As will be described below, the cover 12 is configured to receive an animal 51 (FIG. 6) on the top surface 44 thereof. In this respect, various markings 52 or other insignia may be provided on the top surface 44 of the cover 12 illustrating the proper positioning of the animal 51 thereon. Furthermore, in one embodiment, the cover 12 is formed from a transparent polymer, such as polycarbonate, poly(methyl methacrylate), and/or the like. Nevertheless, in alternative embodiments, the cover 12 may be formed from any other suitable polymer.

As illustrated in FIG. 3, the enclosure 50 may be configured to be at least partially buried within the ground. More specifically, in several embodiments, the enclosure 50 may be positioned within the ground such that at least a portion of the housing 14 is positioned vertically below a ground surface 54. For example, the enclosure 50 may be positioned such that the top surface 44 of the cover 12 is coplanar with the ground surface 54. As will be described below, such positioning of the cover 12 relative to the ground surface 54 permits easy dragging of the animal 51 onto the cover 12. In this respect, in some embodiments, the housing 14 may include a plurality of tabs or wings 56 projecting outwardly (i.e., away from the chamber 42) from the longitudinally-extending walls 32, 34 to support the housing 14 relative to the ground surface 54 such that the top surface 44 of the cover 12 is coplanar with the ground surface 54. Although the housing 14 includes six tabs 56 in the illustrated embodiment, the housing 14 may include more or fewer tabs 56 in other embodiments. Furthermore, the tabs 56 may project outwardly from the transversely-extending walls 36, 38 in addition to or in lieu of the longitudinally-extending walls 32, 34. In alternative embodiments, the enclosure 50 may be positioned entirely above the ground surface 54.

Furthermore, as indicated above, the detection assembly 10 includes the radiation sensor 16. In general, the radiation sensor 16 is configured to detect radiation 57 (FIG. 7) emitted by radionuclides present within the animal 51. For example, in several embodiments, the radiation sensor 16 may include a scintillator 58, such as a sodium iodide (NaI) crystal, and a photomultiplier tube 60. In operation, the scintillator 58 generates photons in response to the radiation 57 received from the animal 51, and the photomultiplier tube 60 converts the photons into an electric signal for processing. Nevertheless, in alternative embodiments, the radiation sensor 16 may be any other device suitable for detecting the radiation 57 emitted by the animal 51. In one embodiment, the radiation sensor 16 may be wrapped or otherwise encased in a polymeric film, such as a polytetrafluoroethylene film, for protection from moisture, dirt, particles, and/or the like.

Figure 5:
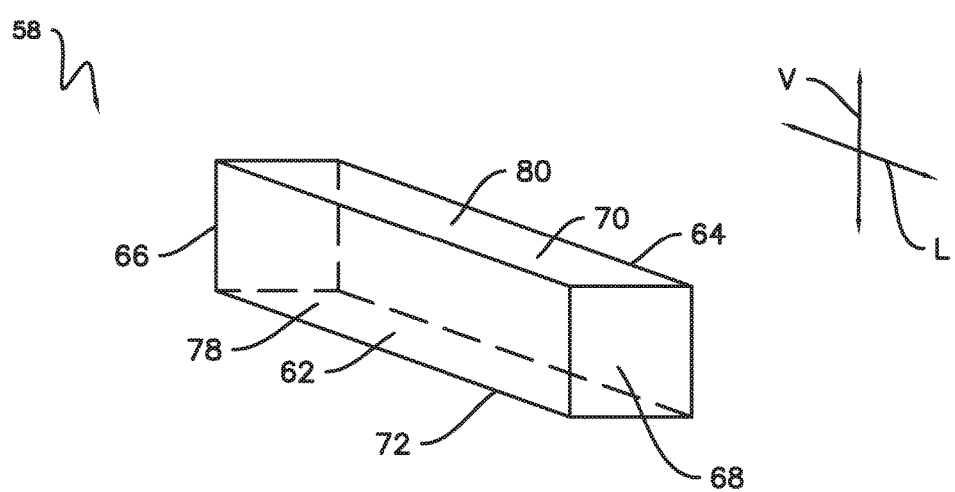
FIG. 5 is a perspective view of a radiation sensor in accordance with aspects of the present disclosure, particularly illustrating various surfaces thereof.
Figure 6:
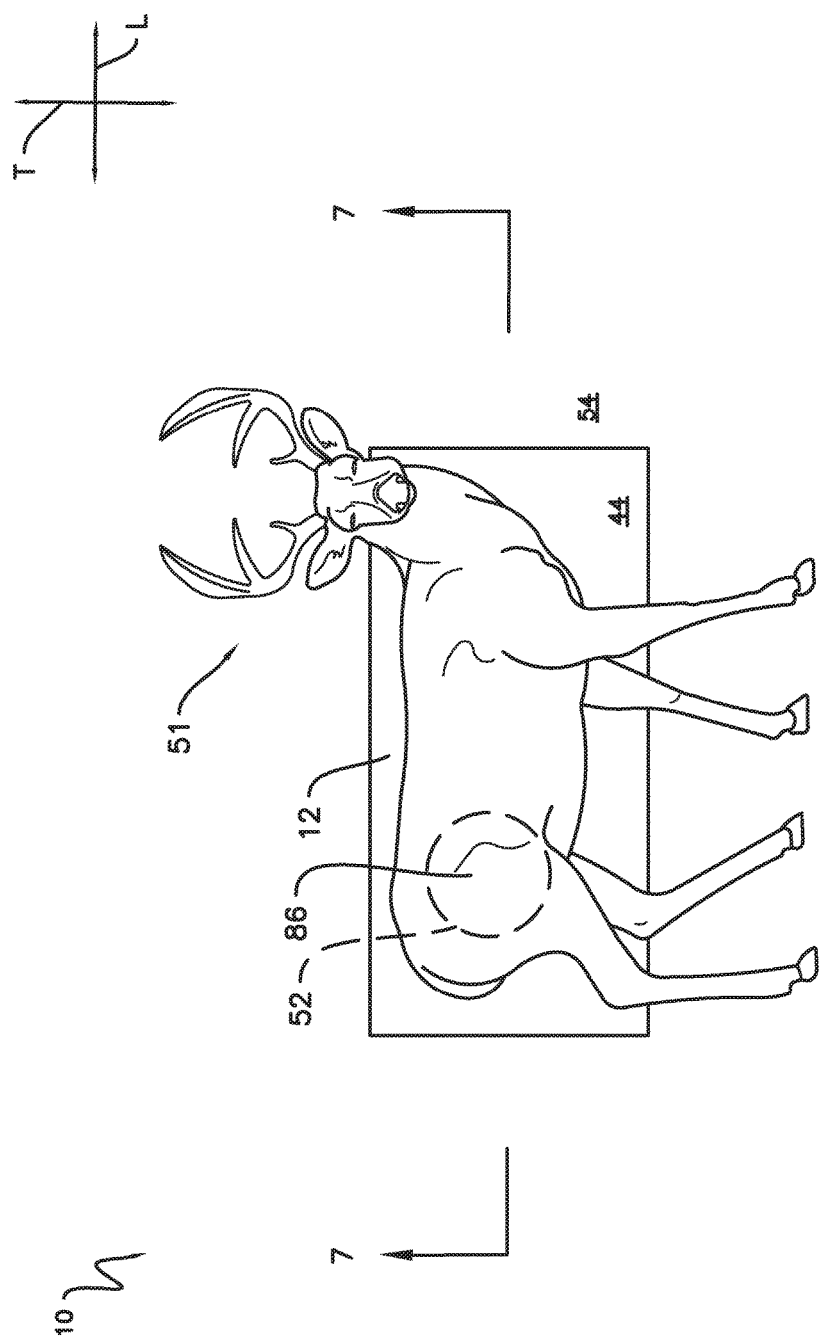
FIG. 6 is a top view of one embodiment of a detection assembly in accordance with aspects of the present disclosure, particularly illustrating an animal positioned on the detection assembly.

Referring now to FIGS. 5 and 6, the scintillator 58 includes various surfaces through which the scintillator 58 may receive incident radiation. For example, in the illustrated embodiment, the scintillator 58 defines a rectangular cuboid shape. As such, the scintillator 58 may include a first longitudinally-extending surface 62 positioned proximate the first longitudinally-extending wall 32 of the housing 14 and a second longitudinally-extending surface 64 positioned proximate the second longitudinally-extending wall 34 of the housing 14. Similarly, the scintillator 58 may include a first transversely-extending surface 66 positioned proximate the first transversely-extending wall 36 of the housing 14 and a second transversely-extending surface 68 positioned proximate to the second transversely-extending wall 38 of the housing 14. Furthermore, the scintillator 58 may include a top surface 70 positioned proximate to the top end 20 of the housing 14 and bottom surface 72 positioned proximate to the bottom wall 40 of the housing 14. Nevertheless, in alternative embodiments, the scintillator 58 may define any other suitable shape and/or include different surfaces in addition to or in lieu of the surfaces 62, 64, 66, 68, 70, 72.

In certain embodiments, as shown in FIGS. 2 and 3, the detection assembly 10 may also include a radiation sensor calibration standard 74 positioned within the chamber 42 of the housing 14. In general, the radiation sensor calibration standard 74 is configured to emit a known quantity of radiation. As such, the radiation sensor 16 may be configured to receive the radiation emitted by the radiation sensor calibration standard 74 and determine its quantity. When properly calibrated, the radiation sensor 16 may determine that the quantity of radiation emitted by the radiation sensor calibration standard 74 within some tolerance (e.g., within ten percent) of its known value. In one embodiment, the radiation sensor calibration standard 74 may include europium-155. However, the radiation sensor calibration standard 74 may include any other suitable radionuclide in other embodiments.

Moreover, as indicated above, the detection assembly 10 further includes the shield 18. In general, the shield 18 is configured to shield, block, or otherwise attenuate at least some environmental radiation 76 incident on the radiation sensor 16 and, more specifically, on the scintillator 58. As used herein, "environmental radiation" includes all radiation incident on the radiation sensor 16 except for the radiation 57 emitted by the animal 51. As such, the shield 18 may be positioned proximate to a first portion 78 of the scintillator 58 to shield the first portion 78 of the scintillator 58 from the environmental radiation 76. Conversely, a second portion 80 of the scintillator 58 is unshielded to permit the scintillator 58 to receive the radiation 57 emitted by the animal 51. As will be described below, the first portion 78 of the scintillator 58 is positioned proximate to the ground or other sources of the environmental radiation 76, while the second portion 80 of the scintillator 58 is positioned proximate to the top end 20 of the housing 14, the cover 12, and the animal 51. Furthermore, the shield 18 may be formed at least partially from lead or another material suitable for shielding or attenuating the environmental radiation 76.

In several embodiments, the shield 18 may be formed from a plurality of shield blocks 82. For example, as shown in FIG. 5, each of the shield blocks 82 may be in contact with or otherwise positioned proximate to one or more of the first and second longitudinally-extending surfaces, the first and second transversely-extending surfaces, and the bottom surface 72 of the scintillator 58. In such embodiments, the surfaces 62, 64, 66, 68, 72 form the first portion 78 (i.e., the shielded portion) of the scintillator 58. In this respect, the shield blocks 82 shield the scintillator 58 from receiving at least some of the environmental radiation 76 through its surfaces 62, 64, 66, 68, 72. Conversely, the top surface 70 forms the second portion 80 (e.g., the unshielded portion) of the scintillator 58. Accordingly, since the animal 51 is positioned on the cover 12 proximate to the unshielded top surface 70, the scintillator 58 is able to receive the radiation 57 emitted by the animal 51. Although the shield 18 includes five shield blocks 82 in the illustrated embodiment, the shield 18 may include any other suitable number of shield blocks 82. For example, in one embodiment, the shield 18 may include as many shield blocks 82 as is necessary to ensure each shield block 82 weighs less than any applicable lifting limits (e.g., 50 pounds).

As illustrated in FIGS. 2 and 3, in one embodiment, the detection assembly 10 may include a base 84. In general, the base 84 may be positioned within the chamber 42 and configured to support the radiation sensor 16. Specifically, the base 84 may be configured to support the scintillator 58 relative to the shield 18. In this respect, the base 84 may be positioned vertically and transversely between the shield 18 and scintillator 58. The base 84 may be constructed from polyethylene or another suitable material. Some embodiments of the detection assembly 10, such as the embodiment shown in FIG. 5, may not include the base 84.

Referring now to FIG. 6, as mentioned above, the cover 12 is configured to receive the animal 51. Specifically, in several embodiments, as shown, the animal 51 is positioned on the top surface 44 of the cover 12 such that its haunch 86 is aligned with the markings 52. In this respect, the haunch 86 of the animal 51 is positioned over the scintillator 58. Furthermore, in one embodiment, the top surface 44 of the cover 12 is coplanar with the ground surface 54, thereby permitting the animal 51 to be dragged onto the cover 12 (e.g., in instances where the animal 51 is too heavy to easily be lifted on the cover 12). Although the animal 51 is illustrated as a deer in FIG. 6, the animal 51 may be a boar, a coyote, a turkey, or any other suitable animal.

Figure 7:
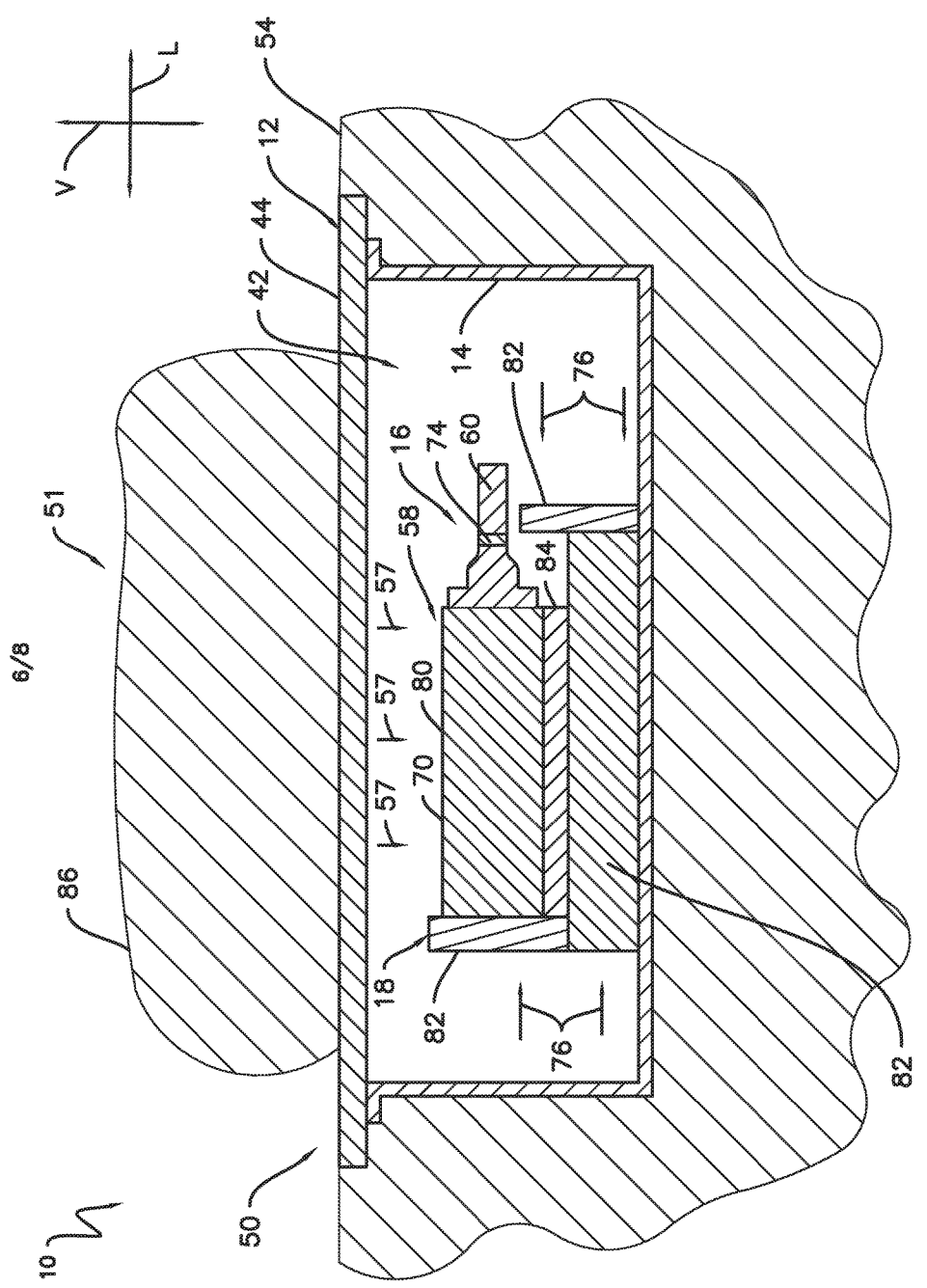
FIG. 7 is a cross-sectional view of the detection assembly taken generally about line 7-7 in FIG. 6, particularly illustrating the radiation sensor detecting radiation emitted by radionuclides present within the animal.

Referring now to FIG. 7, as mentioned above, the radiation sensor 16 is configured to detect the radiation 57 emitted the animal 51. More specifically, the animal 51 may include various radionuclides, such as cesium-137, which emit the radiation 57 (e.g., gamma rays). For example, such radionuclides may be present within the haunch 86 of the animal 51. As shown, after passing through the cover 12, the radiation 57 emitted the radionuclides is received by the top surface 70 (i.e., the unshielded second portion 80) of the scintillator 58. In this respect, the scintillator 70 converts the received radiation 57 into photons, which the photomultiplier tube 60 then converts into an electrical signal. In general, this signal is indicative to the radiation emitted by the radionuclides present in the animal 51. In one embodiment, the scintillator 58 may be configured to detect the radiation emitted by the radiation sensor calibration standard 74 before or after detecting the radiation 57 emitted by the animal 51 to validate the measurement of the radiation 57 emitted by the animal 51.

The shield 18 shields the first portion 78 of the scintillator 58 from receiving at least a portion of the environmental radiation 76 present around the detection device 10. In this respect, the scintillator 58 receives less environmental radiation 76 than conventional radiation sensors. As such, the detection assembly 10, unlike conventional detectors, is able to accurately detect lower levels of radiation emitted by animals than conventional detectors.

Figure 8:
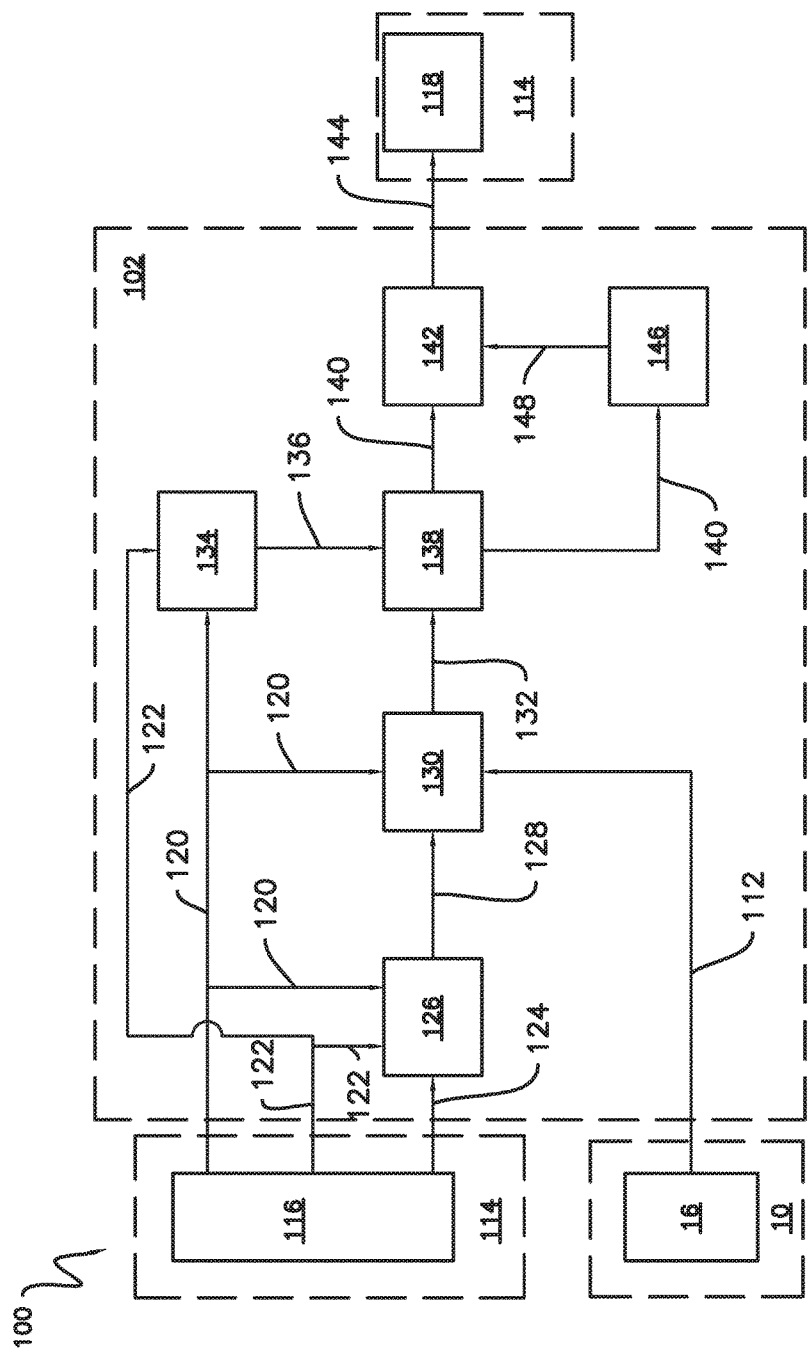
FIG. 8 is a schematic view of one embodiment of a system for determining a radiation dose present within an animal in accordance with aspects of the present disclosure.

FIG. 8 illustrates one embodiment of a system 100 for determining a radiation dose present within an animal. In general, the system 100 will be described herein with reference to the detection assembly 10 and the animal 51 described above. However, the disclosed system 100 may generally be used with detection assemblies and animals having any other suitable configuration.

As shown in FIG. 8, the system 100 may include various components of the detection assembly 10. For example, the system 100 may include the radiation sensor 16 and, more specifically, the scintillator 58 and the photomultiplier tube 60. Nevertheless, in alternative embodiments, the system 100 may include other components of the detection assembly 10 in addition to or lieu of the radiation sensor 16.

Figure 9:
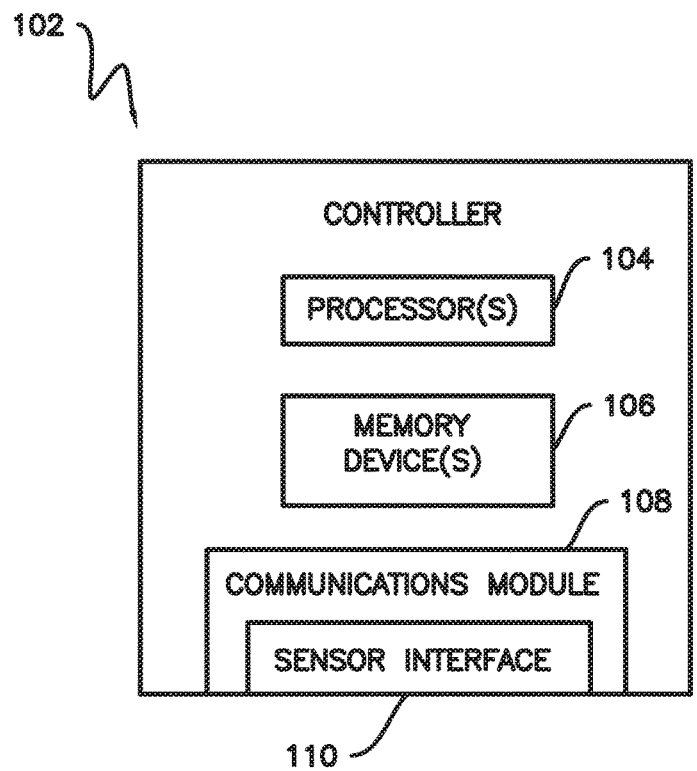
FIG. 9 is a schematic view of a controller of a system for determining a radiation dose present within an animal in accordance with aspects of the present disclosure.

The system 100 also includes a controller 102 communicatively coupled to one or more components of the system 100 and/or the detection assembly 10, such as radiation sensor 16. In general, the controller 102 may correspond to any suitable processor-based device, including one or more computing devices. As shown in FIG. 9, for example, the controller 102 may include one or more processors 104 and one or more associated memory devices 106 configured to perform a variety of computer-implemented functions (e.g., performing the methods, steps, calculations, and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit (ASIC), a Field Programmable Gate Array (FPGA), and other programmable circuits. Additionally, the memory device(s) 106 may generally include memory element(s) including, but not limited to, a computer readable medium (e.g., random access memory (RAM)), a computer readable non-volatile medium (e.g., flash memory), a compact disc-read only memory (CD-ROM), a magneto-optical disk (MOD), a digital versatile disc (DVD), and/or other suitable memory elements or combinations thereof. The memory device(s) 106 may store instructions that, when executed by the processor 104, cause the processor 104 to perform various functions.

The controller 102 may also include a communications module 108 to facilitate communications between the controller 102 and the various components of the system 100 and/or the detection assembly 10. For example, the communications module 108 may permit the controller 102 to receive data from the radiation sensor 16. As such, the communications module 108 may include a sensor interface 110 (e.g., one or more analog-to-digital converters) that converts measurement signals 112 received from the radiation sensor 16 (e.g., the electric signals from the photomultiplier tube 60) into signals that can be understood and processed by the processor(s) 104. In this respect, the communications module 108 may be any combination of suitable wired and/or wireless communication interfaces that communicatively couple radiation sensor 16 to the controller 102.

Referring again to FIG. 8, the system 100 may also include a user interface 114 configured to receive various inputs from an operator of the system 100. As such, the user interface 114 may include one or more input devices 116, such as touchscreens, keypads, touchpads, knobs, buttons, sliders, switches, mice, microphones, and/or the like, configured to receive user inputs from the operator. In addition, the user interface 114 may also include one or more feedback devices 118, such as display screens, speakers, warning lights, and/or the like, configured to communicate the feedback, such as feedback from the controller 102, to the operator of the system 100. However, in alternative embodiments, the user interface 114 may have any suitable configuration.

In several embodiments, the controller 102 may be configured to receive one or more non-geometric parameters indicative of one or more characteristics of the animal 51 from the user interface 114. More specifically, the controller 102 may be communicatively coupled to the user interface 114 via a wired or wireless connection to allow various non-geometric parameter signals to be transmitted from the user interface 114 to the controller 102. For example, as shown, the controller 102 may be configured to receive weight signals (e.g., as indicated by arrow 120 in FIG. 8) indicative of a weight of the animal 51 to be positioned on the cover 12 from the user interface 114. The controller 102 may also be configured to receive animal species signals (e.g., as indicated by arrow 122 in FIG. 8) indicative of a species of the animal 51 (e.g., deer, boar, coyote, etc.) to be positioned on the cover 12 from the user interface 114. Furthermore, the controller 102 may be configured to receive processing status signals (e.g., as indicated by arrow 124 in FIG. 8) indicative of a processing status of the animal 51 (e.g., whether the animal 51 has been dressed) to be positioned on the cover 12 from the user interface 114. Nevertheless, in alternative embodiments, the controller 102 may be configured to receive other non-geometric parameter signals from the user interface 114 in addition to or in lieu of the signals 120, 122, 124.

The controller 102 may be configured to determine one or more geometric parameters of the animal 51 based on the one or more non-geometric parameters. In general, the one or more geometric parameters are related to or associated with the geometry of the animal 51, such its length, girth, shape, and/or geometric profile. As such, the controller 102 may include geometric parameter logic 126 having one or more mathematical functions and/or one or more look-up tables. By executing the geometric parameter logic 126, the controller 102 may determine one or more geometric parameters (e.g., as indicated by arrow 128 in FIG. 8) of the animal 51 based on the received weight, animal species, and processing status signals 120, 122, 124.

Furthermore, the controller 102 may be configured to determine an activity of radionuclides present within the animal 51 based on the one or more of the non-geometric parameters 120, 122, 124; the geometric parameters 128, and/or the measurement signals 112 received from the radiation sensor 16. As such, the controller 102 may include activity logic 130 having one or more mathematical functions and/or one or more look-up tables. By executing the activity logic 130, the controller 102 may determine an activity (e.g., as indicated by arrow 132 in FIG. 8) of the radionuclides within the animal 51 based on the measurement signals 112, the one or more geometric parameters 128, and the weight signals 120.

Moreover, the controller 102 may be configured to determine an adjustment factor based on the one or more of the non-geometric parameter signals 120, 122, 124. In general, the adjustment factor may account the composition of the animal 51, such as the relative proportions of edible meat, bone, skin, etc. For example, in one embodiment, the adjustment factor may be related to the percentage and/or amount of edible meat present within the animal 51. As such, the controller 102 may include adjustment factor logic 134 having one or more mathematical functions and/or one or more look-up tables. By executing the adjustment factor logic 134, the controller 102 may determine an adjustment factor (e.g., as indicated by arrow 136 in FIG. 8) for the animal 51 based on the weight and species signals 120, 122.

The controller 102 may further be configured to determine a single radiation dose quantity one would receive upon consuming the animal 51 based on the one or more of the activity 132 of the radionuclides within the animal 51 and the adjustment factor 136. As such, the controller 102 may include single radiation dose logic 138 having one or more mathematical functions and/or one or more look-up tables. By executing the single radiation dose logic 138, the controller 102 may determine a single radiation dose (e.g., as indicated by arrow 140 in FIG. 8) present within the animal 51 based on the activity 132 and the adjustment factor 136.

Additionally, the controller 102 may be configured initiate a control action based on the determined single radiation dose 140. As such, the controller 102 may include control action logic 142 having one or more mathematical functions and/or one or more look-up tables. By executing the control action logic 142, the controller 102 compares the single radiation dose 140 to a single radiation dose limit and initiates an associated control action based on the comparison. In general, the single radiation dose limit may correspond to a maximum radiation dose that may safely be consumed at one time. When the determined single radiation dose 140 is below the single radiation dose limit, the controller 102 may be configured to transmit suitable feedback signals 144 to the user interface 114 instructing the user interface 114 to provide a visual and/or audible notification indicating that the single radiation dose 140 present within animal 51 is below the single radiation dose limit. Conversely, when the determined single radiation dose 140 is above the single radiation dose limit, the controller 102 may be configured to transmit suitable feedback signals 144 to the user interface 114 instructing the user interface 114 to provide a visual and/or audible notification indicating that the single radiation dose 140 present within animal 51 is above the single radiation dose limit.

Furthermore, in one embodiment, the controller 102 may be configured to determine a total radiation dose received by a hunter or another consumer the animal 51 over a period of time (e.g., a year, a lifetime, etc.). As such, the controller 102 may include total radiation dose logic 146 having one or more mathematical functions and/or one or more look-up tables. By executing the total radiation dose logic 146, the controller 102 may determine a total radiation dose (e.g., as indicated by arrow 148 in FIG. 8) that the hunter or consumer has received over the requisite time period based on the single radiation dose 140 present within the animal 51 and the radiation dose(s) that the hunter or consumer has already received from consuming other animals.

In such embodiment, the controller 102 may be configured initiate a control action based on the determined total radiation dose 148. By executing the control action logic 142, the controller 102 compares the total radiation dose 148 to a total radiation dose limit and initiates an associated control action based on the comparison. In general, the total radiation dose limit may correspond to a maximum radiation dose that may safely be consumed over a particular period of time (e.g., a year, a lifetime, etc.). When the determined total radiation dose 148 is below the total radiation dose limit, the controller 102 may be configured to transmit suitable feedback signals 144 to the user interface 114 instructing the user interface 114 to provide a visual and/or audible notification indicating that the total radiation dose 148 for the hunter or consumer is below the total radiation dose limit. Conversely, when the determined total radiation dose 148 is above the total radiation dose limit, the controller 102 may be configured to transmit suitable feedback signals 144 to the user interface 114 instructing the user interface 114 to provide a visual and/or audible notification indicating that the total radiation dose 140 for the hunter or consumer is above the total radiation dose limit.

As described in greater detail above, the disclosed system 100, unlike conventional systems, is configured to determine a radiation dose present within an animal based on certain geometric parameters, such as length, girth, shape, and/or the like. These geometric parameters are, in turn, determined based on user inputted non-geometric parameters, such as weight and animal species. As such, the system 100 provides a more accurate determination of the radiation dose present within the animal than conventional systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for determining a radiation dose present within an animal, the system comprising:
   a radiation sensor configured to detect radiation emitted by radionuclides present within the animal, the radiation sensor including first portion at least partially shielded from environmental radiation, the radiation sensor further including a second portion that is unshielded to permit the radiation sensor to receive the radiation emitted by the radionuclides present within the animal; and
   a controller communicatively coupled to the radiation sensor, the controller being configured to:
   receive a non-geometric parameter indicative of a characteristic of the animal;
   determine a geometric parameter of the animal based on the non-geometric parameter; and
   determine a radiation dose present within the animal based on the non-geometric parameter, the geometric parameter, and measurement signals received from the radiation sensor.

2. The system of claim 1, wherein the non-geometric parameter comprises at least of one of a weight of the animal, a species of the animal, or a processing status of the animal.

3. The system of claim 1, wherein the geometric parameter comprises at least one of a length of the animal or a girth of the animal.

4. The system of claim 1, wherein the controller is further configured to determine an activity of the radionuclides within the animal based on the non-geometric parameter, the geometric parameter, and the measurement signals received from the radiation sensor.

5. The system of claim 4, wherein the controller is further configured to determine the radiation dose based on the activity and an adjustment factor.

6. The system of claim 5, wherein the controller is further configured to determine the adjustment factor based on the non-geometric parameter.

7. The system of claim 1, wherein the controller is further configured to compare the determined radiation dose to a single dose limit and, when the determined radiation dose exceeds the single dose limit, initiate a control action associated with notifying an operator that the determined radiation dose has exceeded the single dose limit.

8. The system of claim 1, wherein the controller is further configured to determine a current total radiation dose for a consumer based on the determined radiation dose of the animal and a stored previously-received total radiation dose.

9. The system of claim 1, wherein the controller is further configured to compare the current total radiation dose to a total dose limit and, when the determined current total radiation dose exceeds the total dose limit, initiate a control action associated with notifying an operator that the determined current total radiation dose has exceeded the total dose limit.

* * * * *